United States Patent [19]

Steiner

[11] Patent Number: 5,473,080

[45] Date of Patent: Dec. 5, 1995

[54] SUBSTITUTED AZABICYCLOHEPTANE DERIVATIVES, THEIR PREPARATION AND USE

[75] Inventor: Gerd Steiner, Kirchheim, Germany

[73] Assignee: BASF Aktiengesellschaft, Ludwigshafen, Germany

[21] Appl. No.: 351,428

[22] PCT Filed: Jun. 8, 1993

[86] PCT No.: PCT/EP93/01439

§ 371 Date: Dec. 12, 1994

§ 102(e) Date: Dec. 12, 1994

[87] PCT Pub. No.: WO94/00445

PCT Pub. Date: Jan. 6, 1994

[30] Foreign Application Priority Data

Jun. 19, 1992 [DE] Germany .......................... 42 19 975.1

[51] Int. Cl.[6] ...................... C07D 209/02; C07D 401/04
[52] U.S. Cl. ............................ 548/515; 548/466; 546/272
[58] Field of Search ................................... 548/466, 515; 546/272

[56] References Cited

PUBLICATIONS

CA85:159806. Stereoselective . . . olefins. Oppolzer et al., 1976.

Helvetica Chimica ACTA, Bd. 59, Nr. 4, 1976, Oppolzer et 1. Stereoselective syntheses of benz(f) . . . Olefins.

*Primary Examiner*—Joseph K. McKane
*Attorney, Agent, or Firm*—Keil & Weinkauf

[57] ABSTRACT

Novel 3-azabicyclo[3.2.0]heptane derivatives of the formula

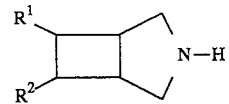

in which $R^1$ and $R^2$ have the meanings stated in the description, and their preparation are described. The substances are intermediates for the preparation of drugs.

5 Claims, No Drawings

SUBSTITUTED AZABICYCLOHEPTANE DERIVATIVES, THEIR PREPARATION AND USE

The present invention relates to novel azabicycloheptane derivatives, their preparation and use for preparing pharmaceutical agents.

The invention relates to 3-azabicyclo[3.2.0]heptane derivatives of the formula I

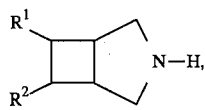

where
$R^1$ is phenyl, pyridyl, thienyl or pyrrolyl which is unsubstituted or mono-or disubstituted by halogen atoms, $C_1$–$C_4$-alkyl, trifluoromethyl, $C_1$–$C_4$-alkoxy, hydroxyl, amino, monomethylamino, dimethylamino, cyano or nitro groups, and $R^2$ is hydrogen or phenyl which is unsubstituted or substituted by fluorine, methoxy, hydroxyl or amino.

Preferred compounds of the formula I are those where $R^2$ is hydrogen and $R^1$ is phenyl which is unsubstituted or substituted by fluorine, chlorine, hydroxyl, methoxy or amino. The phenyl is preferably in the exo configuration.

The compounds of the formula I may also be in the form of salts.

The novel compounds can be prepared by subjecting an amine of the formula II

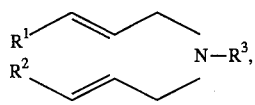

where $R^1$ and $R^2$ have the abovementioned meanings, and $R^3$ is hydrogen, acetyl, trifluoroacetyl or benzyl, to a photochemical 2+2 cycloaddition and eliminating any acyl or benzyl group $R^3$.

The photoreaction takes place well in an inert solvent, preferably acetone, at from 20° to 80° C. A particularly suitable light source is a high-pressure mercury lamp. It may be advantageous to carry out the photocycloaddition in a quartz apparatus under a nitrogen atmosphere with or without the addition of about 1 mole of hydrochloric acid per mole of amine.

X-ray structural analysis shows that the photocycloaddition in most cases takes place highly diastereoselectively to give the bicyclic compounds I with the exo configuration in respect of $R^1$ and $R^2$:

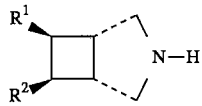

The two enantiomers can be isolated pure by racemate resolution, eg. using optically active tartaric acid derivatives.

The amines of the formula II are disclosed in the literature or can be prepared by either reacting an aldehyde $R^1$—CHO with vinylmagnesium chloride to give the allyl alcohol III

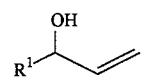

subsequently rearranging with hydrogen chloride to the allyl chloride IV

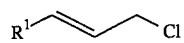

and finally substituting with the appropriate allylamine V

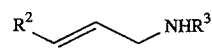

or subjecting a cinnamaldehyde VI

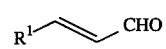

directly to reductive amination with the allylamine V.

The elimination of an acyl radical from the compounds II is expediently carried out by conventional methods of hydrolysis, Similar is true of the elimination of the benzyl radical.

The compounds of the formula I according to the invention are valuable intermediates in the synthesis of novel pharmacologically active compounds of the formulae VII and VIII

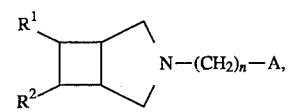

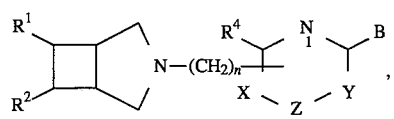

where
$R^1$ and $R^2$ have the stated meanings,
n is 1, 2, 3 or 4,
A is hydrogen or one of the radicals

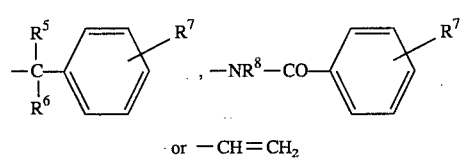

(where
$R^5$ is hydrogen, hydroxyl or phenyl which is unsubstituted or substituted by a fluorine, chlorine or bromine atom,
$R^6$ is hydrogen, or
$R^5$ and $R^6$ together are an oxygen atom,
$R^7$ is hydrogen, fluorine, chlorine, bromine, hydroxyl, nitro, $C_1$–$C_4$-alkyl or methoxy,
$R^8$ is hydrogen or methyl)
$R^4$ is hydrogen, hydroxyl, $C_1$–$C_4$-alkyl or $C_1$–$C_4$-alkoxy, or together with the adjacent carbon atom is a C=O or C=S group,
X and Y are carbon atoms, CH, $CH_2$, NH or $C_1$–$C_4$-alkyl-N groups or nitrogen atoms,
Z is a direct linkage, a CO group, CS group or a CH or CH$_2$ group in which a hydrogen in atom can be replaced by a hydroxyl, amino or C$_1$–C$_4$-alkoxy group or a halogen atom, and B is hydrogen, hydroxyl, amino, mercapto, C$_1$–C$_4$-alkylamino, di-C$_1$–C$_4$-alkylamino, C$_1$–C$_4$-alkylthio or C$_1$–C$_4$-alkoxy, or together with the adjacent carbon atom is a C=O group, or is a C$_3$–C$_4$-alkylene group which is linked to Y and which may contain one or two non-cumulative double bonds and in which one CH or CH$_2$ group can be replaced by a nitrogen or sulfur atom or an NH or N-CH$_3$ group, and where the ring can be monosubstituted either by a fluorine or chlorine atom or a methyl, methoxy, nitro or amino group, or in the case of a benzene ring the latter can be mono-, di- or trisubstituted by fluorine or chlorine atoms or methyl, trifluoromethyl, nitro, hydroxyl, methoxy, amino, monomethyl- or dimethylamino groups, and in which the ring in the right-hand part of the formula VIII can carry a C$_1$–C$_4$-alkyl, allyl or benzyl group on nitrogen atom No. 1 and may contain 1 to 3 non-cumulative double bonds, and their salts with physiologically tolerated acids.

The compounds of the formulae VII and VIII are obtained from the compounds I by reacting with compounds of the formulae IX and X

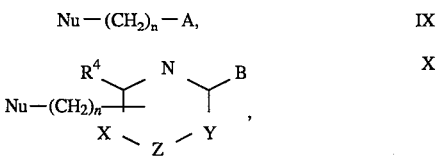

where Nu is a nucleofugic leaving group, for example a halogen atom, in particular a bromine or chlorine atom, and A, B, X, Y, Z, R$^4$ and n have the abovementioned meanings. The reaction expediently takes place in an inert solvent such as tetrahydrofuran, toluene or xylene in the presence of an inert base such as potassium carbonate or triethylamine at 80° to 150° C.

The compounds of the formulae VII and VIII have valuable pharmacological properties, for example as neuroleptics, antidepressants, sedatives, hypnotics, CNS protectives or muscle relaxants.

The following examples serve to illustrate the invention.

A Preparation of the starting materials

1. N-Cinnamyl-N-allylamine 175 ml (1.27 mol) of triethylamine were added to 173 ml (1.16 mol) of cinnamyl chloride in 1,350 ml of tetrahydrofuran, the mixture was heated to 60° C., and then 105 ml (1.40 mol) of allylamine were added dropwise. The mixture was refluxed for 6 h and then stirred at room temperature for 10 h. After concentration under water pump vacuum, the contents of the flask were partitioned between methyl t-butyl ether and water (pH=10). The aqueous phase was extracted twice more with methyl t-butyl ether and subsequently the combined organic phases were extracted with a mixture of 250 ml of concentrated hydrochloric acid and 2 l of water. The aqueous phase was then extracted with 1.2 l of methylene chloride, and the methylene chloride phase washed five times with 500 ml of 10% strength hydrochloric acid each time. The combined aqueous phases were made alkaline with concentrated sodium hydroxide solution and extracted twice with methylene chloride. Drying and concentration of the organic phase resulted in 66.5 g of crude product which was distilled at 86°–88° C. under oil pump vacuum (0.25 mbar). Yield: 64 g (32%).

2. N-Cinnamylbenzylamine and bis(N-cinnamyl)benzylamine 113 ml (818 mmol) of triethylamine were added to 96.4 g (600 mmol) of cinnamyl chloride in 800 ml of tetrahydrofuran, the mixture was heated to 60° C., and then 65.4 ml (600 mmol) of benzylamine were added dropwise. The mixture was refluxed for 3 h and then stirred at room temperature for 15 h. After concentration under water pump vacuum, the contents of the flask were partitioned between methyl t-butyl ether and water (pH=10). The organic phase was washed twice with water, dried with sodium sulfate and concentrated. The crude product (109 g) composed of mono- and bisadduct was dissolved in 400 ml of acetone, a solution of 48 g (413 mmol) of maleic acid in 250 ml of acetone was added while stirring and, after cooling, the precipitated solid was filtered off with suction. After washing with acetone, 60.0 g (30%) of N-cinnamylbenzylamine were isolated as maleate, melting point 169°–170° C.

The mother liquor was completely evaporated and the residue was stirred with ethyl acetate overnight. After cooling in ice, the precipitated solid was filtered off with suction and washed with ethyl acetate. 65.0 g (48%) of bis(N-cinnamyl)benzylamine were isolated as maleate, oil.

3. N-Cinnamyl-N-allylbenzylamine 11.0 g (90 mmol) of allyl bromide were added to 10.0 g (44.8 mmol) of N-cinnamylbenzylamine in 60 ml of ethanol, and then 5.0 g (50.0 mmol) of triethylamine were added while stirring. The mixture was refluxed for 4 h. Concentration under water pump vacuum was followed by partition of the contents of the flask between methylene chloride and water, rendition alkaline with dilute sodium hydroxide solution and extraction twice more with methylene chloride. The combined organic phases were washed with dilute sodium hydroxide solution, dried and concentrated. The crude product (12.5 g) was purified by column chromatography (silica gel, mobile phase methylene chloride/methanol 98/2). 9.2 g (80%) of product (oil) were obtained.

4. 1-(4-Fluorophenyl)allyl alcohol 1,550 ml (2.0 mol) of a 1.29 M solution of vinylmagnesium chloride in tetrahydrofuran were introduced into a 4 l stirred flask under nitrogen. Subsequently, while stirring under nitrogen at 30°–35° C., a solution of 222.0 g (1,764 mol) of 4-fluorobenzaldehyde in 2,000 ml of tetrahydrofuran was added over the course of 30 min, cooling the reaction mixture with ice. The mixture was then stirred at room temperature under nitrogen for 2.5 h. Subsequently, while stirring and cooling with ice, 180 ml of water were added, the mixture was filtered with suction, and the residue from the filter was washed 3x with 150 ml of tetrahydrofuran. The filtrates were combined, dried with sodium sulfate and concentrated. 265.7 g (99%) of product were obtained in the form of a yellow-brown oil.

5. 3-(4-Fluorophenyl)allyl chloride 273.6 g (1.798 mol) of 1-(4-fluorophenyl)allyl alcohol were dissolved with stirring in 2,000 ml of methylene chloride. Subsequently, 101.0 g (2,770 mol) of hydrogen chloride were passed in over the course of 3 h, during which the temperature rose to 37° C. The mixture was then stirred for 1 h. After washing with 600 ml of ice-cold water and a mixture of 150 ml of saturated brine and 150 ml of water, the organic phase was dried over sodium sulfate and concentrated. 294.6 g (98%) of a brown oil were obtained.

6. N-Allyl-N-[3-(4-fluorophenyl)allyl]amine 231.8 g (1.359 mol) of 3-(4-fluorophenyl)allyl chloride were added over the course of 25 min to a refluxing solution of 795.0 g (13.92 mol) of allylamine in 360 ml of toluene, and the mixture was then refluxed for 1 h. 1,000 ml were then distilled out through a 10 cm distillation column (5 mm glass rings) at a bath temperature up to 125° C. 1,000 ml of water were added to the distillation residue, and the pH was adjusted to 0.7 with 38% strength hydrochloric acid. The organic phase was separated off and discarded. The aqueous phase was adjusted to pH 12.7 with 50% strength sodium hydroxide solution and was extracted with toluene. The toluene extracts were dried with sodium sulfate and concentrated.

The residue was distilled through a column under 0.7–1 mbar at a bath temperature of 120°–160° C. to afford 191.8 g (74%) of a pale yellow oil.

7. N-Allyl-N-[3-(3,5-dichlorophenyl)allyl]amine 4.5 ml (60 mmol, 3.4 g) of allylamine and 17.0 g of sodium sulfate were added to 12.0 g (59.7 mmol) of 3,5-dichlorocinnamaldehyde in 180 ml of methylene chloride, and the mixture was stirred at room temperature for 24 h. The sodium sulfate was then filtered and washed with methylene chloride, and the filtrate was evaporated to dryness. The resulting yellow oil was dissolved in 200 ml of absolute methanol and, under nitrogen, 2.5 g (66.0 mmol) of sodium borohydride were added in portions. The temperature of the mixture rose slightly and it was then stirred for 1 h and subsequently neutralized (pH=7) with 10% strength hydrochloric acid. The solvent was removed under reduced pressure, and the residue was taken up in methylene chloride. The organic phase was washed twice with water, dried over sodium sulfate and concentrated. The residue was purified by column chromatography (silica gel, methylene chloride +5% methanol). Yield: 9.2 g (63%) of yellow oil.

8. N-Allyl-2,2,2-trifluoro-N-[3-(3-pyridyl)allyl]acetamide 16.1 g (76.6 mmol) of trifluoroacetic anhydride were slowly added dropwise to a solution of 10.0 g (57.5 mmol) of N-allyl-N-[3-(3-pyridyl)allyl]amine and 10.7 ml of triethylamine in 100 ml of tetrahydrofuran at 0° C. The mixture was then stirred at room temperature for 2 h. The solution was subsequently poured into 250 ml of ice-water and extracted three times with 150 ml of methyl tertbutyl ether each time. The combined organic phases were dried over sodium sulfate and concentrated: 14.3 g (92%) of dark brown oil.

B Preparation of the final products 1. exo-6-(p-Fluorophenyl)-3-azabicyclo[3.2.0]heptane 130 ml of 10% strength hydrochloric acid and 600 mg of Michler's ketone were added to 19.4 g (102 mmol) of N-allyl-N-[3-(4-fluorophenyl)allyl]amine in 130 ml of acetone, and the mixture was irradiated in a quartz apparatus under nitrogen at room temperature with a 150 watt high-pressure mercury lamp for 55 h. The mixture was subsequently concentrated, and the residue was partitioned between methylene chloride and water. The aqueous phase was made alkaline with aqueous ammonia solution and extracted twice more with methylene chloride. The combined organic phases were dried with sodium sulfate and concentrated. Yield 19.3 g (99%), melting point 165°–166° C. (maleate).

To separate the antipodes, 15.0 g (78.5 mmol) of the racemate were mixed with a solution of 31.7 g (78.5 mmol) of (−)-di-O-toluoyl-L-tartaric acid in 300 ml of boiling ethanol. The crystals which separated out on cooling while stirring (13.8 g) were filtered off with suction, washing with ethanol, and recrystallized from 300 ml of ethanol with the addition of 200 ml of water. Liberation of the base provided the (+) antipode (5.5 g) with $[\alpha]_D=+97.0°0$(EtOH, c=0.969).

14.2 g of a salt crystallized out of the above mother liquor overnight and were recrystallized from 400 ml of ethanol (insolubles removed by filtering at the boiling point) (concentration to 300 ml). Liberation of the base provided 4.0 g of the (−) antipode with $[\alpha]_D=96.0°$ (EtOH, c=0.940).

The exo-phenyl configurations were demonstrated by X-ray structural analysis.

2. exo-6-Phenyl-3-azabicyclo[3.2.0]heptane 300 ml of 10% strength hydrochloric acid were added to 50.0 g (28.9 mmol) of N-cinnamyl-N-allylamine in 1,600 ml of acetone, and the mixture was irradiated in a quartz apparatus at room temperature under nitrogen with a 150 watt high-pressure mercury lamp for 48 h. The mixture was then concentrated, and the residue was partitioned between methylene chloride and water. The aqueous phase was made alkaline with aqueous ammonia solution and extracted twice more with methylene chloride. The combined organic phases were dried with sodium sulfate and concentrated. Yield 49.0 g (98%) of viscous oil, melting point 177°–178° C. (maleate).

3. exo-6,7-Diphenyl-3-benzyl-3-azabicyclo[3.2.0]heptane 0.8 g of Michler's ketone was added to 70.0 g (206 mmol) of bis(N-cinnamyl)benzylamine in 2,500 ml of acetone, and the mixture was irradiated in a Duran glass apparatus at room temperature under nitrogen with a 150 watt high-pressure mercury lamp for 25 h. The mixture was then concentrated, and the residue was partitioned between methylene chloride and water. The aqueous phase was made alkaline with aqueous ammonia solution and extracted twice more with methylene chloride. The combined organic phases were dried with sodium sulfate and concentrated. The crude product (65.0 g) was purified by column chromatography (silica gel, mobile phase toluene/ethanol 98/2). 58.0 g (83%) of product were obtained, melting point 230°–232° C. (hydrochloride).

4. exo-6,7-Diphenyl-3-azabicyclo[3.2.0]heptane 16.0 g (254 mmol) of ammonium formate and 2.0 g of palladium (10%) on carbon were added to 12.0 g (35.4 mmol) of exo-6,7-diphenyl-3-benzyl-3-azabicyclo[3.2.0]heptane in a mixture of 300 ml of n-propanol and 16 ml of water, and the mixture was refluxed for 4 h (evolution of carbon dioxide). After cooling, the catalyst was filtered off with suction and washed with propanol and methylene chloride, and the filtrate was concentrated. The residue was partitioned between methylene chloride and water, and the aqueous phase was made alkaline with aqueous ammonia solution and extracted twice more with methylene chloride. The combined organic phases were dried with sodium sulfate and concentrated. 8.1 g (92%) of product were obtained, melting point 140°–142° C. (maleate).

5. exo-6-Phenyl-3-benzyl-3-azabicyclo[3.2.0]heptane 100 mg of Michler's ketone were added to 9.2 g (35.0 mmol) of N-cinnamyl-N-allylbenzylamine in 1,100 ml of acetone, and the mixture was irradiated in a Duran glass apparatus at room temperature under nitrogen with a 150 watt high-pressure mercury lamp for 5 h. The mixture was then concentrated. The crude product (9.4 g) was purified by column chromatography (silica gel, mobile phase methylene chloride/methanol 98/2). 3.3 g (36%) of product were obtained, melting point 126°–128° C. (maleate).

6. 2,2,2-Trifluoro-1-[exo-6-(3-pyridyl) -3-azabicyclo [3.2.0 ] -hept-3-yl]ethanone 14.0 g (51.8 mmol) of N-allyl-2,2,2-trifluoro-N-[3-(3-pyridyl)allyl]acetamide were dissolved in 140 ml of acetone, 30 ml of 10% strength aqueous hydrochloric acid were added, and the mixture was irradiated in a Duran glass apparatus at room temperature under nitrogen with a 150 watt high-pressure mercury lamp for 48 h. The solution was then concentrated, the residue was taken up in 150 ml of water, and the mixture was adjusted to pH 8–9 with aqueous ammonia solution. The aqueous phase was extracted twice with tert-butyl methyl ether, and the combined organic phases were dried over sodium sulfate and concentrated. The residue was fractionated by column chromatography (silica gel, methylene chloride +2% methanol) to yield 6.2 g (42%) of unchanged N-allyl-2,2,2-trifluoro-N-[3-(3-pyridyl)allyl] acetamide and 3.7 g (26%) of 2,2,2-trifluoro-1-[exo-6-(3-pyridyl)-3-azabicyclo[3.2.0]hept-3-yl]ethanone as dark oil.

7. exo-6-(3-Pyridyl)-3-azabicyclo[3.2.0]heptane 2.5 g of potassium hydroxide pellets were added to a solution of 3.7 g (13.7 mmol) of 2,2,2-trifluoro-1-[exo-6-(3-pyridyl)-3-azabicyclo[3.2.0]hept-3-yl]ethanone in 50 ml of ethanol. The solution was stirred at room temperature for 2 h and then poured into 100 ml of ice-water. The aqueous phase was extracted three times with tert-butyl methyl ether, and the combined organic phases were dried over sodium sulfate and concentrated. Yield 2.3 g (96%) of yellow oil, melting point 202°–205° C. (hydrochloride).

The following final products can be prepared in a similar way:

8. exo-6-(m-Fluorophenyl)-3-azabicyclo[3.2.0]heptane,
9. exo-6-(o-Fluorophenyl)-3-azabicyclo[3.2.0]heptane, melting point 118°–120° C. (maleate)
10. exo-6-(p-Chlorophenyl)-3-azabicyclo[3.2.0]heptane, melting point 152°–154° C. (maleate)
11. exo-6-(m-Chlorophenyl)-3-azabicyclo[3.2.0]heptane melting point 130°–132° C. (maleate)
12. exo-6-(p-Methoxyphenyl)-3-azabicyclo[3.2.0]heptane
13. exo-6-(m-Methoxyphenyl)-3-azabicyclo[3.2.0]heptane
14. exo-6-(p-Nitrophenyl)-3-azabicyclo[3.2.0]heptane melting point 158°–160° C. (maleate)
15. exo-6-(m-Nitrophenyl)-3-azabicyclo[3.2.0]heptane
16. exo-6-(p-Trifluoromethyl-phenyl)-3-azabicyclo-[3.2.0]heptane, melting point 155°–156° C. (maleate)
17. exo-6-(m-Trifluoromethyl-phenyl)-3-azabicyclo-[3.2.0]heptane
18. exo-6-(3,4-Dichlorophenyl)-3-azabicyclo[3.2.0]-heptane
19. exo-6-(3,5-Dichlorophenyl)-3-azabicyclo[3.2.0]-heptane, melting point >250° C. (hydrochloride)
20. exo-6-(3,4-Dimethoxy-phenyl)-3-azabicyclo[3.2.0]-heptane
21. exo-6-(m-Hydroxyphenyl)-3-azabicyclo[3.2.0]heptane
22. exo-6-(p-Hydroxyphenyl)-3-azabicyclo[3.2.0]heptane
23. exo-6-(3,4-Dihydroxyphenyl)-3-azabicyclo[3.2.0]-heptane
24. exo-6-(p-Methylphenyl)-3-azabicyclo[3.2.0]heptane
25. exo-6-(m-Methylphenyl)-3-azabicyclo[3.2.0]heptane
26. exo-6-(p-t-Butylphenyl)-3-azabicyclo[3.2.0]heptane, melting point >255° C. (hydrochloride)
27. exo-6-(m-Aminophenyl)-3-azabicyclo[3.2.0]heptane
28. exo-6-(p-Aminophenyl)-3-azabicyclo[3.2.0]heptane
29. exo-6-(p-Cyanophenyl)-3-azabicyclo[3.2.0]heptane, melting point 168°–170° C. (maleate)
30. exo-6-(2-Thienyl)-3-azabicyclo[3.2.0]heptane, melting point 180°–182° C. (hydrochloride)
31. exo-6-(3-Thienyl)-3-azabicyclo[3.2.0]heptane, melting point 143°–145° C. (hydrochloride)
32. exo-6-(5-Chloro 2-thienyl)-3-azabicyclo[3.2.0]-heptane, melting point 156°–157° C. (maleate)
33. exo-6-(2-Pyrrolyl)-3-azabicyclo[3.2.0]heptane
34. exo-6-(4-Pyridyl)-3-azabicyclo[3.2.0]heptane
35. exo-6-(2-Pyridyl)-3-azabicyclo[3.2.0]heptane.

I claim:

1. A 3-azabicyclo(2.3.0)heptane derivative of the formula I

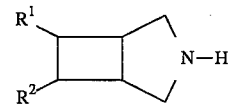

where $R^1$ is phenyl, pyridyl, thienyl or pyrrolyl which is unsubstituted or mono- or disubstituted by halogen atoms, $C_1$–$C_4$-alkyl, trifluoromethyl, $C_1$–$C_4$-alkoxy, hydroxyl, amino, monomethylamino, dimethylamino, cyano or nitro groups, and $R^2$ is hydrogen.

2. A 3-azabicyclo(2.3.0)heptane derivative of the formula I as defined in claim 1, wherein $R^1$ is phenyl which is unsubstituted or mono- or disubstituted by halogen atoms, $C_1$–$C_4$-alkyl, trifluoromethyl, $C_1$–$C_4$-alkoxy, hydroxyl, amino, monomethylamino, dimethylamino, cyano or nitro groups.

3. A 3-azabicyclo(2.3.0)heptane derivative of the formula I as defined in claim 1, wherein $R^1$ is unsubstituted phenyl.

4. A 3-azabicyclo(2.3.0)heptane derivative of the formula I as defined in claim 1, wherein $R^1$ is phenyl substituted by fluorine or chlorine.

5. A 3-azabicyclo(2.3.0)heptane derivative of the formula I as defined in claim 1, wherein $R^1$ is phenyl substituted by methoxy.

* * * * *